| United States Patent [19] | [11] Patent Number: 4,978,804 |
| Woell | [45] Date of Patent: Dec. 18, 1990 |

[54] PROCESSES FOR THE CONVERSION OF MYRCENE TO CITRAL

[75] Inventor: James B. Woell, Lawrenceville, N.J.

[73] Assignee: Union Camp Corporation, Wayne, N.J.

[21] Appl. No.: 363,808

[22] Filed: Jun. 9, 1989

Related U.S. Application Data

[63] Continuation-in-part of Ser. No. 269,278, Nov. 9, 1988.

[51] Int. Cl.$^5$ .............................................. C07C 45/00
[52] U.S. Cl. ................................... 568/489; 568/449; 568/484; 568/485
[58] Field of Search ............... 568/484, 485, 489, 448, 568/449, 489

[56] References Cited

U.S. PATENT DOCUMENTS 4,347,387 8/1982 Akutagawa ......................... 568/489

FOREIGN PATENT DOCUMENTS 624222 7/1961 Canada ................................. 568/490

Primary Examiner—Werren B. Lone
Attorney, Agent, or Firm—Edward J. Sites

[57] ABSTRACT

A novel process for converting myrcene to citral using palladium (II) chloride in the presence of an inert aqueous alkylamide solvent and a metal oxoanionic salt at a temperature of at least about 80° C. is disclosed. A novel process for converting a palladium-myrcene complex to citral using a metal oxoanionic salt in the presence of an inert aqueous organic solvent is also disclosed.

24 Claims, No Drawings

PROCESSES FOR THE CONVERSION OF MYRCENE TO CITRAL

RELATED APPLICATION

This application is a continuation-in-part of copending application U.S. Ser. No. 269,278 filed Nov. 9, 1988 pending.

BACKGROUND OF THE INVENTION

The availability of adequate supplies of monoterpene aldehydes, particularly citral, is an issue of great importance to a number of industries. Although some processes for the commercial production of citral are available, new and/or improved synthetic routes are needed.

Organometallic chemistry has been used by a number of researchers in an attempt to effect various monoterpene transformations. Early experiments are reported in McQuillin et al., *J. Chem. Soc. Perkin Trans. I*, pp. 809–815 (1974), and Dunne et al., *J. Chem. Soc. (C)*. pp. 2196–2200, 2200–2203, and 2203–2206 (1970). In these studies, the authors prepared several allyl palladium complexes of terpene compounds, including those resulting from the reaction of palladium with myrcene. Cyclization of myrcene, however, was found to occur, and citral was never obtained from the described processes.

Adding to this earlier work, Takahashi et al., *Journal of Organometallic Chemistry*, Vol. 266, pp. 327–336 (1984) successfully prepared a mixture of citral and nerol utilizing a two-step method. First, myrcene was reacted with dichlorobis(acetonitrile)palladium in the solvent hexamethylphosphoric triamide (HMPA) or in the presence of a base such as $Li_2CO_3$ using dimethylformamide (DMF) as solvent, to yield a non-cyclized palladium-myrcene complex. Although the reported yield for the HMPA process was relatively good, the $Li_2CO_3$/DMF process yield was somewhat low, approximately 33%. In the second step of the reported process, the complex was isolated, and then treated with base to yield terpene aldehydes and alcohols such as citral and nerol. One major drawback of these processes, however, is that they necessitate two steps, requiring isolation of the intermediate before further processing. Moreover, the product obtained using these methods is a mixture of both citral and nerol. Furthermore, the reactions are saddled with the added disadvantage of a temperature limitation, since at temperatures above about 60° C. the solvents HMPA and DMF are decomposed by the palladium species. See Bombieri et al., *Inorganica Chimica Acta*, Vol. 86, pp. 121–125 (1984); Fahey et al., *Journal of Organic Chemistry*, Vol. 39, pp. 3276–77 (1974). In addition, the use of HMPA in this, or any process, is clearly undesirable, since HMPA is an extremely potent toxin, as well as a suspected carcinogen.

Citral is a compound of high significance to the flavor, fragrance and synthetic vitamin industries. Additional and/or better processes for their commercial production, particularly processes employing the readily available starting material myrcene, are needed. The present invention is directed to this very important end.

SUMMARY OF THE INVENTION

The present invention provides a novel and highly efficient one-step process for the production of citral comprising contacting myrcene with palladium (II) chloride in the presence of an inert aqueous alkylamide solvent and a metal oxoanionic salt at a temperature of at least about 80° C. Preferably, the process is carried out in the presence of an oxidizing agent.

The present invention also provides a process for producing citral comprising contacting a palladium-myrcene complex of the formula

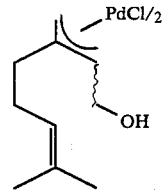

with a metal oxoanionic salt in the presence of an inert aqueous organic solvent. Preferably, the process is carried out at a temperature of at least about 80° C.

Using the foregoing processes, myrcene production can be efficiently and effectively carried out with a high yield of and high selectivity to this very important end product.

DETAILED DESCRIPTION OF THE INVENTION

The subject invention involves the production of the monoterpene aldehyde citral (that is, 3,7-dimethyl-(E,Z)-2,6-octadienal), a compound of significant importance to the flavor, fragrance and synthetic vitamin industries. Specifically, in one aspect, the present invention provides a process for the direct production of citral comprising contacting myrcene with palladium (II) chloride in the presence of an inert aqueous amide solvent and a metal oxoanionic salt at a temperature of at least about 80° C.

The myrcene employed in the subject processes may be pure myrcene or other suitable mixtures of compounds containing myrcene, as will be apparent to those skilled in the art. One readily available and relatively inexpensive source of myrcene is a myrcene and limonene mixture in a ratio of about 80 to about 20, respectively, a product which is commercially available. Since myrcene is relatively unstable to oxygen, it is preferable to utilize a myrcene mixture containing a antioxidant such as 2,6-di-tertiary-butyl-4-methylphenol, commonly referred to as butylated hydroxy toluene (BHT) and sold under the tradename Ionol by Shell Chemical Company, New York, N.Y.

The palladium (II) chloride may be added directly as $PdCl_2$. Alternatively, it may be formed in situ by the addition of a source of chloride ion, such as LiCl or NaCl, to a palladium (II) salt, such as $PdSO_4$, $Pd(NO_3)_2$, $Pd_3(PO_4)_2$ and $Pd(BF_4)_2$. Other sources of chloride ion and palladium (II) salts suitable for in situ generation of the palladium (II) chloride will be apparent to those skilled in the art. If desired, the $PdCl_2$ compound may be complexed with loosely coordinated ligand donors, such as acetonitrile, benzonitrile, 1,5-cyclooctadiene and dimethyl sulfoxide. Thus, the palladium (II) chloride may be in the form of, for example, dichlorobisacetonitrile palladium, that is, $PdCl_2(CH_3CN)_2$. Other suitable ligand donors for coordination with the $PdCl_2$ compound will be apparent to those skilled in the art. These and other obvious variations are intended to be within the ambit of the phrase palladium (II) chloride, as used herein. Preferably, the palladium (II) chloride is PdCl$_2$ or PdCl$_2$(CH$_3$CN)$_2$.

As used herein, the term "inert", employed in connection with the phrase "aqueous alkylamide solvent" denotes those aqueous alkylamide solvents which are substantially unreactive with palladium species under the conditions of the subject process. Suitable inert aqueous alkylamide solvents include those alkylamide solvents wherein the alkylamide is fully substituted. Examples include substituted aqueous pyrrolidones such as aqueous N-methyl-pyrrolidone and aqueous N-ethylpyrrolidone, substituted aqueous caprolactams such as aqueous N-methylcaprolactam, and substituted aqueous acetamides such as aqueous N,N-dimethylacetamide, aqueous N,N-diethylacetamide, as well as aqueous N,N-dimethylpropionamide and aqueous N,N-diethylpropionamide. Other suitable inert aqueous alkylamide solvents will be apparent to those skilled in the art. Preferably, the inert aqueous alkylamide solvent is aqueous N-methylyrrolidone, a compound of the formula

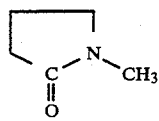

Not only does aqueous N-methylpyrrolidone promote the appropriate and efficient conversion of myrcene to citral, it also lacks the toxic and carcinogenic properties found in HMPA.

Any of the variety of metal oxoanionic salts available may be employed in the present process. Preferable metal oxoanionic salts include Li$_2$B$_4$O$_7$, Li$_2$B$_{10}$O$_{16}$, Li$_2$SiO$_3$, Li$_3$PO$_4$, Li$_2$WO$_4$, Li$_2$CrO$_4$, Li$_2$MoO$_4$, LiTiO$_3$, LiCoO$_2$, Li$_2$CO$_3$, Li$_2$SO$_4$, Li$_2$SnO$_3$, Li$_3$VO$_4$, Li$_2$TeO$_4$, Na$_2$B$_4$O$_7$, Na$_2$B$_{10}$O$_{16}$, Na$_2$SiO$_3$, Na$_3$PO$_4$, Na$_2$WO$_4$, Na$_2$CrO$_4$, Na$_2$MoO$_4$, NaTiO$_3$, NaCoO$_2$, Na$_2$CO$_3$, Na$_2$SO$_4$, Na$_2$SnO$_3$, Na$_3$VO$_4$, Na$_2$TeO$_4$, K$_2$B$_4$O$_7$, K$_2$B$_{10}$O$_{16}$, K$_2$SiO$_3$, K$_3$PO$_4$, K$_2$WO$_4$, K$_2$CrO$_4$, K$_2$MoO$_4$, KTiO$_3$, KCoO$_2$, K$_2$CO$_3$, K$_2$SO$_4$, K$_2$SnO$_3$, K$_3$VO$_4$, K$_2$TeO$_4$, MgB$_4$O$_7$, MgB$_{10}$O$_{16}$, MgSiO$_3$, Mg$_3$(PO$_4$)$_2$, MgWO$_4$, MgCrO$_4$, MgMoO$_4$, Mg(TiO$_3$)$_2$, Mg(CoO$_2$)$_2$, MgCO$_3$, MgSO$_4$, CaB$_4$O$_7$, CaB$_{10}$O$_{16}$, CaSiO$_3$, Ca$_3$(PO$_4$)$_2$, CaWO$_4$, CaCrO$_4$, Ca(TiO$_3$)$_2$, Ca(CoO$_2$)$_2$, CaCO$_3$, CaSO$_4$, Cu$_2$B$_4$O$_7$, Cu$_2$B$_{10}$O$_{16}$, Cu$_2$SiO$_3$, Cu$_3$PO$_4$, Cu$_2$WO$_4$, Cu$_2$CrO$_4$, Cu$_2$MoO$_4$, CuTiO$_3$, CuCoO$_2$, Cu$_2$CO$_3$, Cu$_2$SO$_4$, CuB$_4$O$_7$, CuB$_{10}$O$_{16}$, CuSiO$_3$, Cu$_3$(PO$_4$)$_2$, CuWO$_4$, CuCrO$_4$, CuMoO$_4$, Cu(TiO$_3$)$_2$, Cu(CoO$_2$)$_2$, CuCO$_3$, CuSO$_4$, Ag$_2$B$_4$O$_7$, Ag$_2$B$_{10}$O$_{16}$, Ag$_2$SiO$_3$, Ag$_3$PO$_4$, Ag$_2$WO$_4$, Ag$_2$CrO$_4$, AgTiO$_3$, AgCoO$_2$, Ag$_2$CO$_3$, Ag$_2$SO$_4$, Al$_2$(B$_4$O$_7$)$_3$, Al$_2$(B$_{10}$O$_{16}$)$_3$, Al$_2$(SiO$_3$)$_3$, AlPO$_4$, Al$_2$(WO$_4$)$_3$, Al$_2$(CrO$_4$)$_3$, Al$_2$(MoO$_4$)$_3$, Al(TiO$_3$)$_3$, Al(CoO$_2$)$_3$, Al$_2$(CO$_3$)$_3$, Al$_2$(SO$_4$)$_3$, SnB$_4$O$_7$, SnB$_{10}$O$_{16}$, SnSiO$_3$, Sn$_3$(PO$_4$)$_2$, SnWO$_4$, SnCrO$_4$, SnMoO$_4$, Sn(TiO$_3$)$_2$, Sn(CoO$_2$)$_2$, SnCO$_3$, SnSO$_4$, Sn(B$_4$O$_7$)$_2$, Sn(B$_{10}$O$_{16}$)$_2$, Sn(SiO$_3$)$_2$, Sn$_3$(PO$_4$)$_4$, Sn(WO$_4$)$_2$, Sn(CrO$_4$)$_2$, Sn(MoO$_4$)$_2$, Sn(TiO$_3$)$_4$, Sn(CoO$_2$)$_4$, Sn(CO$_3$)$_2$, Sn(SO$_4$)$_2$, PdB$_4$O$_7$, PdB$_{10}$O$_{16}$, PdSiO$_3$, Pd$_3$(PO$_4$)$_2$, PdWO$_4$, PdCrO$_4$, PdMoO$_4$, Pd(TiO$_3$)$_2$, Pd(CoO$_2$)$_2$, PdCO$_3$, PdSO$_4$, Pd(B$_4$O$_7$)$_2$, Pd(B$_{10}$O$_{16}$)$_2$, and Pd(SiO$_3$)$_2$.

More preferably, the metal oxoanionic salt is selected from the group consisting of Li$_2$B$_4$O$_7$, Li$_2$B$_{10}$O$_{16}$, Li$_2$SiO$_3$, Li$_2$TeO$_4$, Li$_2$SnO$_3$, Li$_2$MoO$_4$, Li$_3$VO$_4$, Na$_2$B$_4$O$_7$, Na$_2$B$_{10}$O$_{16}$, Na$_2$SiO$_3$, Na$_2$SnO$_3$, Na$_2$MoO$_4$, Na$_2$TeO$_4$, Na$_3$VO$_4$, K$_2$B$_4$O$_7$, K$_2$B$_{10}$O$_{16}$, K$_2$SiO$_3$, K$_2$SnO$_3$, K$_2$MoO$_4$, K$_3$VO$_4$, K$_2$TeO$_4$, MgB$_4$O$_7$, MgB$_{10}$O$_{16}$, MgSiO$_3$, MgMoO$_4$, Cu$_2$B$_4$O$_7$, Cu$_2$B$_{10}$O$_{16}$, Cu$_2$SiO$_3$, Cu$_2$MoO$_4$, CuB$_4$O$_7$, CuB$_{10}$O$_{16}$, CuSiO$_3$, CuMoO$_4$, SnB$_4$O$_7$, SnB$_{10}$O$_{16}$, SnSiO$_3$, SnMoO$_4$, Sn(B$_4$O$_7$)$_2$, Sn(B$_{10}$O$_{16}$)$_2$, Sn(SiO$_3$)$_2$ and Sn(MoO$_4$)$_2$. Most preferably, the metal oxoanionic salt is selected from the group consisting of Na$_2$MoO$_4$, Li$_2$MoO$_4$ and K$_2$MoO$_4$.

As one skilled in the art will recognize, such salts may, if desired, be formed in situ.

The amount of myrcene, palladium (II) chloride, metal oxoanionic salt and solvent employed in the foregoing process can vary widely, as will be recognized by those skilled in the art. By way of guidance, however, palladium (II) chloride is preferably present in a molar amount equal to about 0.1 to about 0.6 times the molar amount of myrcene employed. Metal oxoanionic salt is preferably present in a molar amount equal to about 4 to about 10 times the molar amount of the palladium (II) chloride utilized. The inert aqueous alkylamide solvent preferably comprises about 70% to about 90% of the total reaction mixture volume, the aqueous solvent itself being comprised of about 70% to about 90% of solvent and a corresponding amount of about 10% to about 30% of water on a total aqueous solvent volume basis.

The foregoing reaction requires temperatures of at least about 80° C., proceeding best at temperatures of at least about 90° C. The reaction may be conducted at atmospheric pressure, and generally runs to completion within a few hours. To maximize yields, slow but continual stirring, such as by use of a magnetic stirrer, may be employed. If desired, the reaction may be carried out in an inert atmosphere, such as in the presence of, for example, nitrogen, carbon dioxide, or argon gas.

In a preferable embodiment, the foregoing process is carried out in the presence of an oxidizing agent. Such oxidizing agents include, for example, hydrogen peroxide, benzoquinone, copper (II) salts such as copper chloride, cerium (IV) salts, iron (III) salts and silver (I) salts. Other suitable oxidizing agents will be apparent to those skilled in the art. As a skilled artisan would recognize, where copper (II) or iron (III) salts are employed, for example, oxygen or air may, if desired, be introduced into the reaction vessel to assist in reoxidation of the metal salts. Preferably, the oxidizing agent is selected from the group consisting of hydrogen peroxide, benzoquinone and copper (II) salts, particularly copper chloride. Most preferably, the oxidizing agent is hydrogen peroxide or copper (II) salts, particularly copper chloride.

The amount of oxidizing agent employed can vary widely as will be readily apparent to those skilled in the art. Preferably, the oxidizing agent is added in a molar amount equal to about 1 to about 5 times the molar amount of the palladium (II) chloride utilized.

The present invention further contemplates a process for producing citral comprising contacting a palladium-myrcene complex of the formula

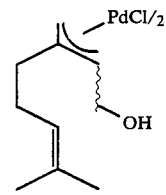

with a metal oxoanionic salt in the presence of an inert aqueous organic solvent.

The palladium-myrcene complex employed can be obtained by using a number of different methods known to those skilled in the art, such as the methods disclosed in Takahashi et al., *Journal of Organometallic Chemistry*, Vol. 266, pp. 327–336 (1984). The palladium-myrcene complex can also be produced using the processes described in copending application U.S. Ser. No. 269,278, filed on Nov. 9, 1988, and entitled "Processes for the Conversion of Myrcene to Nerol and Citral", the disclosures of which are incorporated by reference herein.

Any of the variety of metal oxoanionic salts available may be employed in the present process. Preferable metal oxoanionic salts include $Li_2B_4O_7$, $Li_2B_{10}O_{16}$, $Li_2SiO_3$, $Li_3PO_4$, $Li_2WO_4$, $Li_2CrO_4$, $Li_2MoO_4$, $LiTiO_3$, $LiCoO_2$, $Li_2CO_3$, $Li_2SO_4$, $Li_2SnO_3$, $Li_3VO_4$, $Li_2TeO_4$, $Na_2B_4O_7$, $Na_2B_{10}O_{16}$, $Na_2SiO_3$, $Na_3PO_4$, $Na_2WO_4$, $Na_2CrO_4$, $Na_2MoO_4$, $NaTiO_3$, $NaCoO_2$, $Na_2CO_3$, $Na_2SO_4$, $Na_2SnO_3$, $Na_3VO_4$, $Na_2TeO_4$, $K_2B_4O_7$, $K_2B_{10}O_{16}$, $K_2SiO_3$, $K_3PO_4$, $K_2WO_4$, $K_2CrO_4$, $K_2MoO_4$, $KTiO_3$, $KCoO_2$, $K_2CO_3$, $K_2SO_4$, $K_2SnO_3$, $K_3VO_4$, $K_2TeO_4$, $MgB_4O_7$, $MgB_{10}O_{16}$, $MgSiO_3$, $Mg_3(PO_4)_2$, $MgWO_4$, $MgCrO_4$, $MgMoO_4$, $Mg(TiO_3)_2$, $Mg(CoO_2)_2$, $MgCO_3$, $MgSO_4$, $CaB_4O_7$, $CaB_{10}O_{16}$, $CaSiO_3$, $Ca_3(PO_4)_2$, $CaWO_4$, $CaCrO_4$, $Ca(TiO_3)_2$, $Ca(CoO_2)_2$, $CaCO_3$, $CaSO_4$, $Cu_2B_4O_7$, $Cu_2B_{10}O_{16}$, $Cu_2SiO_3$, $Cu_3PO_3$, $Cu_2WO_4$, $Cu_2CrO_3$, $Cu_2MoO_4$, $CuTiO_3$, $CuCoO_2$, $Cu_2CO_3$, $Cu_2SO_4$, $CuB_4O_7$, $CuB_{10}O_{16}$, $CuSiO_3$, $Cu_3(PO_4)_2$, $CuWO_4$, $CuCrO_4$, $CuMoO_4$, $Cu(TiO_3)_2$, $Cu(CoO_2)_2$, $CuCO_3$, $CuSO_4$, $Ag_2B_4O_7$, $Ag_2B_{10}O_{16}$, $Ag_2SiO_3$, $Ag_3PO_4$, $Ag_2WO_4$, $Ag_2CrO_4$, $AgTiO_3$, $AgCoO_2$, $Ag_2CO_3$, $Ag_2SO_4$, $Al_2(B_4O_7)_3$, $Al_2(B_{10}O_{16})_3$, $Al_2(SiO_3)_3$, $AlPO_4$, $Al_2(WO_4)_3$, $Al_2(CrO_4)_3$, $Al_2(MoO_4)_3$, $Al(TiO_3)_3$, $Al(CoO_2)_3$, $Al_2(CO_3)_3$, $Al_2(SO_4)_3$, $SnB_4O_7$, $SnB_{10}O_{16}$, $SnSiO_3$, $Sn_3(PO_4)_2$, $SnWO_4$, $SnCrO_4$, $SnMoO_4$, $Sn(TiO_3)_2$, $Sn(CoO_2)_2$, $SnCO_3$, $SnSO_4$, $Sn(B_4O_7)_2$, $Sn(B_{10}O_{16})_2$, $Sn(SiO_3)_2$, $Sn_3(PO_4)_4$, $Sn(WO_4)_2$, $Sn(CrO_4)_2$, $Sn(MoO_4)_2$, $Sn(TiO_3)_4$, $Sn(CoO_2)_4$, $Sn(CO_3)_2$, $Sn(SO_4)_2$, $PdB_4O_7$, $PdB_{10}O_{16}$, $PdSiO_3$, $Pd_3(PO_4)_2$, $PdWO_4$, $PdCrO_4$, $PdMoO_4$, $Pd(TiO_3)_2$, $Pd(CoO_2)_2$, $PdCO_3$, $PdSO_4$, $Pd(B_4O_7)_2$, $Pd(B_{10}O_{16})_2$, and $Pd(SiO_3)_2$.

More preferably, the metal oxoanionic salt is selected from the group consisting of $Li_2B_4O_7$, $Li_2B_{10}O_{16}$, $Li_2SiO_3$, $Li_2MoO_4$, $Na_2B_4O_7$, $Na_2B_{10}O_{16}$, $Na_2SiO_3$, $Na_2MoO_4$, $K_2B_4O_7$, $K_2B_{10}O_{16}$, $K_2SiO_3$, $K_2MoO_4$, $MgB_4O_7$, $MgB_{10}O_{16}$, $MgSiO_3$, $MgMoO_4$, $Cu_2B_4O_7$, $Cu_2B_{10}O_{16}$, $Cu_2SiO_3$, $Cu_2MoO_4$, $CuB_4O_7$, $CuB_{10}O_{16}$, $CuSiO_3$, $CuMoO_4$, $SnB_4O_7$, $SnB_{10}O_{16}$, $SnSiO_3$, $SnMoO_4$, $Sn(B_4O_7)_2$, $Sn(B_{10}O_{16})_2$, $Sn(SiO_3)_2$ and $Sn(MoO_4)_2$. Most preferably, the metal oxoanionic salt is selected from the group consisting of $Li_2B_4O_7$, $Li_2B_{10}O_{16}$, $K_2B_4O_7$ and $K_2B_{10}O_{16}$.

As one skilled in the art would recognize, such salts may, if desired, be formed in situ.

As used herein, the term "inert," employed in connection with the phrase "aqueous organic solvent", denotes those aqueous organic solvents which are substantially unreactive with the palladium species under the conditions of the subject process. Suitable inert aqueous organic solvents include substituted aqueous pyrrolidones such as aqueous N-methylpyrrolidone and aqueous N-ethylpyrrolidone, substituted aqueous caprolactams such as aqueous N-methylcaprolactam, substituted aqueous acetamides such as aqueous N,N-dimethylacetamide, aqueous N,N-diethylacetamide, and also aqueous N,N-dimethylpropionamide and N,N-diethylpropionamide, and substituted and unsubstituted toluene in water. Other suitable solvents will be readily apparent to those skilled in the art. Preferably, the inert aqueous organic solvent is aqueous N-methylpyrrolidone or toluene in water.

The amount of palladium-myrcene complex, metal oxoanionic salt and solvent employed in the foregoing process can vary widely, as will be recognized by those skilled in the art. By way of guidance, however, the metal oxoanionic salt is preferably employed in a molar amount equal to about 5 to about 20 times the molar amount of palladium-myrcene complex employed. The inert aqueous organic solvent preferably comprises about 70% to about 90% of the total reaction mixture volume, the aqueous solvent itself being comprised of about 70% to about 90% of solvent, and a corresponding about 10% to about 30% of water on a total aqueous solvent volume basis.

Preferably, the reaction is carried out at a temperature of at least about 80° C., most preferably at a temperature of at least about 90° C.

The foregoing processes clearly provide efficient and commercially viable pathways to the important compound citral.

The citral compound produced by the subject processes is useful in a variety of ways, for example, it may be employed as a fragrance or a flavor additive or as a precursor for the synthesis of vitamins A and E. See Derfer et al., "Terpenoids", pp. 709–762 in *Kirk-Othmer Encyclopedia of Chemical Technology*, 3rd ed., Vol. 22, Wiley Interscience Publications (New York, 1983), the disclosures of which are incorporated by reference herein.

The present invention is further described in the following Examples. These Examples are not to be construed as limiting the scope of the appended claims.

EXAMPLES

In the Examples which follow, the myrcene employed was a myrcene and limonene mixture in a ratio of about 80 to about 20, respectively, obtained from Aldrich Chemical Company, Milwaukee, Wis.

The resulting products were analyzed using gas chromatography (GC), and yield and selectivity results recorded. Yield calculations in all of the Examples were based on the initial level of the palladium (II) salt. Selectivity data is based on the amount of consumed myrcene. The amount of citral produced and the amount of myrcene remaining were measured by internal standard weight % GC.

EXAMPLE 1

To a solution of N-methylpyrrolidone (0.75 ml) and $Li_2MoO_4$ (0.11 gm) was added $PdCl_2(CH_3CN)_2$ (0.03 gm) and water (0.075 ml). The solution was gently but continuously stirred using a magnetic stirrer for about 5 minutes while nitrogen was employed as an inert purging gas. Myrcene (0.066 ml) was then added to the solution and the mixture was heated to about 90° C. for about 2.5 hrs, with gentle and continuous stirring. Tridecane (0.014 gm) was then added to the mixture as an internal standard, and the solution was transferred to a separation funnel. Toluene (1.5 ml) was added, and the solution was extracted five times using a $NaCl/H_2O$ mixture. The organic phase was then dried over $K_2CO_3$.

The resulting yield of citral was 44%, with a selectivity of 26%.

EXAMPLE 2

The procedures of Example 1 were substantially followed except that $LiTiO_3$ (0.077 gm) was utilized in lieu of $Li_2MoO_4$.

The resulting yield of citral was 39%, with a selectivity of 22%.

EXAMPLE 3

The procedures of Example 1 were substantially followed except that $LiCoO_2$ (0.065 gm) was utilized in lieu of $Li_2MoO_4$.

The resulting yield of citral was 29%, with a selectivity of 16%.

EXAMPLE 4

The procedures of Example 1 were substantially followed except that $Li_2CO_3$ (0.047 gm) was utilized in lieu of $Li_2MoO_4$.

The resulting yield of citral was 35%, with a selectivity of 25%.

EXAMPLE 5

The procedures of Example 1 were substantially followed except that $Li_2SO_4$ (0.084 gm) was utilized in lieu of $Li_2MoO_4$.

The resulting yield of citral was 14%, with a selectivity of 8%.

EXAMPLE 6

To a solution of N-methylpyrrolidone (0.75 ml) and $Li_2MoO_4$ (0.11 gm) was added $PdSO_4$ (0.024 gm), LiCl (0.0054 gm), benzoquinone (0.03 gm) and $H_2O$ (0.075 ml). The solution was gently but continuously stirred for about 5 minutes using nitrogen as an inert purging gas. Myrcene (0.066 ml) was added and the solution was heated to about 90° C., for about 2.5 hrs, with gentle and continuous stirring. Tridecane (0.013 gm) was then added to the mixture as an internal standard, and the solution was transferred to a separation funnel, rinsed with toluene (1.5 ml) and extracted five times using a $NaCl/H_2O$ solution. The organic phase was then dried over $K_2CO_3$, and the resulting product analyzed substantially as described in Example 1.

The resulting yield of citral was 34%, with a selectivity of 17%.

EXAMPLE 7

The procedures of Example 6 were substantially followed except that $PdCl_2(CH_3CN)_2$ (0.03 gm) was employed in lieu of $PdSO_4$ and LiCl, and $CuCl_2$ (0.015 gm) was utilized instead of benzoquinone.

The resulting yield of citral was 53%, with a selectivity of 28%.

EXAMPLE 8

The procedures of Example 7 were substantially followed except that the amount of $PdCl_2(CH_3CN)_2$, $Li_2MoO_4$, $CuCl_2$, N-methylpyrrolidine and water were increased 10-fold, and the reaction was carried out a temperature of about 80° C.

The resulting yield of citral was 54%, with a selectivity of 28%.

EXAMPLE 9

The procedures of Example 8 were substantially followed except that the solution was heated at about 80° C. for a total of about 5 hours, instead of 2.5 hours.

The resulting yield of citral was 62%, with a selectivity of 32%.

EXAMPLE 10

The procedures of Example 8 were substantially followed except that oxygen was bubbled through the solution at a rate of about 52 ml per minute following addition of myrcene.

The resulting yield of citral was 19%, with a selectivity of 9%.

EXAMPLE 11

The procedures of Example 9 were substantially followed except that after heating for the indicated 5 hours at 80° C., the solution was refrigerated overnight, and then heated to about 80° C. for about 7 additional hours.

The resulting yield of citral was 70%, with a selectivity of 35%.

EXAMPLE 12

The procedures of Example 11 were substantially followed except that after heating for the indicated additional 7 hours at 80° C., the solution was refrigerated overnight without a cap, and then heated to about 80° C. under an inert nitrogen atmosphere for about 2.5 additional hours.

The resulting yield of citral was 49%, with a selectivity of 32%.

EXAMPLE 13

The procedures of Example 6 were substantially followed except that $PdCl_2(CH_3CN)_2$ (0.03 gm) was utilized in lieu of $PdSO_4$ and LiCl, $Li_2WO_4$ (0.17 gm) was utilized in lieu of $Li_2MoO_4$, and $H_2O_2$ (0.075 ml) was utilized in lieu of benzoquinone and $H_2O$, and the solution was heated to about 80° C. instead of 90° C.

The resulting yield of citral was 33%, with a selectivity of 23%.

EXAMPLE 14

The procedures of Example 6 were substantially followed except that $PdCl_2(CH_3CN)_2$ (0.03 gm) was utilized in lieu of $PdSO_4$ and LiCl, 0.21 gm of $Li_2MoO_4$ was employed, and 30% $H_2O_2$ (0.75 ml) was utilized in lieu of benzoquinone and water.

The resulting yield of citral was 52%, with a selectivity of 26%.

EXAMPLE 15

To an isolated palladium-myrcene complex (0.048 gm) was added $Li_2B_4O_7$ (0.11 gm), N-methylpyrrolidone (1.5 ml) and $H_2O$ (0.150 ml). The mixture was heated to about 70° C. for about 1.5 hours with gentle but continuous stirring. Tridecane (0.012 gm) was added to the mixture as an internal standard, and the solution was transferred to a separation funnel, rinsed with toluene (1.5 ml) and extracted five times using a $NaCl/H_2O$ solution. The resulting product was then analyzed substantially as described in Example 1.

The resulting yield of citral was 27%.

EXAMPLE 16

The procedures of Example 15 were substantially followed except that 0.025 gm of the palladium-myrcene complex, 0.750 ml of N-methylpyrrolidone, and 0.075 ml of $H_2O$ were employed, and the solution was heated to about 90° C.

The resulting yield of citral was 45%.

EXAMPLE 17

The procedures of Example 15 were substantially followed except that 0.025 gm of the palladium-myrcene complex, 0.75 ml of N-methylpyrrolidone, and 0.075 ml of $H_2O$ were employed, and $Li_2SiO_3$ (0.059 gm) was utilized in lieu of $Li_2B_4O_7$.

The resulting yield of citral was 30%.

EXAMPLE 18

The procedures of Example 15 were substantially followed except that 0.026 gm of the palladium-myrcene complex, 0.75 ml of N-methylpyrrolidone, and 0.075 ml of $H_2O$ were utilized, and $K_2B_4O_7$ (0.15 gm) was employed in lieu of $Li_2B_4O_7$.

The resulting yield of citral was 45%.

EXAMPLE 19

The procedures of Example 15 were substantially followed except that 0.024 gm of the palladium-myrcene complex, 0.75 ml of N-methylpyrrolidone, and 0.075 ml of $H_2O$ were employed, and $K_2B_{10}O_{16}$ was utilized in lieu of $Li_2B_4O_7$.

The resulting yield of citral was 41%.

EXAMPLE 20

To a solution of N-methylpyrrolidone (7.5 ml) and $K_2MoO_4$ (1.51 gm) was added $PdCl_2(CH_3CN)_2$ (0.30 gm), Ionol (0.0005 gm) (available from Shell Chemical Company, New York, N.Y.) and $H_2O$ (0.75 ml). The solution was gently but continuously stirred for about 5 minutes using carbon dioxide as an inert purging gas. Myrcene (669 ml) was then added to the solution and the mixture was heated to about 90° C. for about 2.5 hours, with gentle and continuous stirring. Tridecane (0.108 gm) was then added to the mixture as an internal standard, and the solution was transferred to a separation funnel, rinsed with toluene (15 ml) and extracted 5 times using a $NaCl/H_2O$ solution. The organic phase was then dried over $K_2CO_3$, and the resulting product analyzed substantially as described in Example 1.

The resulting yield of citral was 53%, with a selectivity of 29%.

EXAMPLE 21

The procedures of Example 20 were substantially followed except that $Na_2MoO_4$ (1.53 gm) was employed in lieu of $K_2MoO_4$, and 0.0006 gm of Ionol was utilized.

The resulting yield of citral was 49%, with a selectivity of 28%.

EXAMPLE 22

The procedures of Example 20 were substantially followed except that $PdCl_2$ (0.20 gm) was employed in lieu of $PdCl_2(CH_3CN)_2$, $MgMoO_4$ (1.16 gm) was employed in lieu of $K_2MoO_4$, and 0.0006 gm of Ionol were utilized.

The resulting yield of geranial was 14%, with a selectivity of 10%.

Various modifications of the invention in addition to those shown and described herein will be apparent to those skilled in the art from the foregoing description. Such modifications are also intended to fall within the scope of the appended claims.

What is claimed is:

1. A process for producing citral comprising contacting myrcene with palladium (II) chloride in the presence of an inert aqueous alkylamide solvent and a metal oxoanionic salt at a temperature of at least about 80° C.

2. A process according to claim 1 wherein said temperature is at least about 90° C.

3. A process according to claim 1 wherein the palladium (II) chloride is selected from the group consisting of $PdCl_2$ and $PdCl_2$ loosely coordinated with ligand donors.

4. A process according to claim 3 wherein the ligand donors are selected from the group consisting of acetonitrile, benzonitrile, 1,5-cyclooctadiene and dimethyl sulfoxide.

5. A process according to claim 4 wherein the palladium (II) chloride is dichlorobisacetonitrile palladium.

6. A process according to claim 1 wherein the inert aqueous amide solvent is selected from the group consisting of N-substituted aqueous pyrrolidones, N-substituted aqueous caprolactams and N,N-disubstituted aqueous alkylamides.

7. A process according to claim 6 wherein the solvent is a substituted aqueous pyrrolidone which is aqueous N-methylpyrrolidone.

8. A process according to claim 1 wherein the metal oxoanionic salt is selected from the group consisting of $Li_2B_4O_7$, $Li_2B_{10}O_{16}$, $Li_2SiO_3$, $Li_3PO_4$, $Li_2WO_4$, $Li_2CrO_4$, $Li_2MoO_4$, $LiTiO_3$, $LiCoO_2$, $Li_2CO_3$, $Li_2SO_4$, $Li_2SnO_3$, $Na_2B_4O_7$, $Na_2B_{10}O_{16}$, $Na_2SiO_3$, $Na_2SnO_3$, $Na_3VO_4$, $Na_3PO_4$, $Na_2WO_4$, $Na_2CrO_4$, $Na_2MoO_4$, $NaTiO_3$, $NaCoO_2$, $Na_2CO_3$, $Na_2SO_4$, $Na_2TeO_4$, $K_3VO_4$, $K_2B_4O_7$, $K_2B_{10}O_{16}$, $K_2SiO_3$, $K_2SnO_3$, $K_3PO_4$, $K_2WO_4$, $K_2CrO_4$, $K_2MoO_4$, $KTiO_3$, $K_2SnO_3$, $K_2TeO_4$, $KCoO_2$, $K_2CO_3$, $K_2SO_4$, $MgB_4O_7$, $MgB_{10}O_{16}$, $MgSiO_3$, $Mg_3(PO_4)_2$, $MgWO_4$, $MgCrO_4$, $MgMoO_4$, $Mg(TiO_3)_2$, $Mg(CoO_2)_2$, $MgCO_3$, $MgSO_4$, $CaB_4O_7$, $CaB_{10}O_{16}$, $CaSiO_3$, $Ca_3(PO_4)_2$, $CaWO_4$, $CaCrO_4$, $Ca(TiO_3)_2$, $Ca(CoO_2)_2$, $CaCO_3$, $CaSO_4$, $Cu_2B_4O_7$, $Cu_2B_{10}O_{16}$, $Cu_2SiO_3$, $Cu_3PO_4$, $Cu_2WO_4$, $Cu_2CrO_4$, $Cu_2MoO_4$, $CuTiO_3$, $CuCoO_2$, $Cu_2CO_3$, $Cu_2SO_4$, $CuB_4O_7$, $CuB_{10}O_{16}$, $CuSiO_3$, $Cu_3(PO_4)_2$, $CuWO_4$, $CuCrO_4$, $CuMoO_4$, $Cu(TiO_3)_2$, $Cu(CoO_2)_2$, $CuCO_3$, $CuSO_4$, $Ag_2B_4O_7$, $Ag_2B_{10}O_{16}$, $Ag_2SiO_3$, $Ag_3PO_4$, $Ag_2WO_4$, $Ag_2CrO_4$, $AgTiO_3$, $AgCoO_2$, $Ag_2CO_3$, $Ag_2SO_4$, $Al_2(B_4O_7)_3$, $Al_2(B_{10}O_{16})_3$, $Al_2(SiO_3)_3$, $AlPO_4$, $Al_2(WO_4)_3$, $Al_2(CrO_4)_3$, $Al_2(MoO_4)_3$, $Al(TiO_3)_3$, $Al(CoO_2)_3$, $Al_2(CO_3)_3$, $Al_2(SO_4)_3$, $SnB_4O_7$, $SnB_{10}O_{16}$, $SnSiO_3$, $Sn_3(PO_4)_2$, $SnWO_4$, $SnCrO_4$, $SnMoO_4$, $Sn(TiO_3)_2$, $Sn(CoO_2)_2$, $SnCO_3$, $SnSO_4$, $Sn(B_4O_7)_2$, $Sn(B_{10}O_{16})_2$, $Sn(SiO_3)_2$, $Sn_3(PO_4)_4$, $Sn(WO_4)_2$, $Sn(CrO_4)_2$, $Sn(MoO_4)_2$, $Sn(TiO_3)_4$, $Sn(CoO_2)_4$, $Sn(CO_3)_2$, $Sn(SO_4)_2$, $PdB_4O_7$, $PdB_{10}O_{16}$, $PdSiO_3$, $Pd_3(PO_4)_2$, $PdWO_4$, $PdCrO_4$, $PdMoO_4$, $Pd(TiO_3)_2$, $Pd(CoO_2)_2$, $PdCO_3$, $PdSO_4$, $Pd(B_4O_7)_2$, and $Pd(B_{10}O_{16})_2$.

9. A process according to claim 8 wherein the metal oxoanionic salt is selected from the group consisting of $Li_2B_4O_7$, $Li_2B_{10}O_{16}$, $Li_2SiO_3$, $Li_2MoO_4$, $Li_2SO_4$, $Li_2CO_3$, $Li_2TeO_4$, $Li_3PO_4$, $Na_2B_4O_7$, $Na_2B_{10}O_{16}$, $Na_2SiO_3$, $Na_2SnO_3$, $Na_2MoO_4$, $Na_2TeO_4$, $Na_3PO_4$, $Na_3VO_4$, $K_2TeO_4$, $K_2B_4O_7$, $K_2B_{10}O_{16}$, $K_2CO_3$, $K_2SiO_3$, $K_2SnO_3$, $K_2MoO_4$, $K_3VO_4$, $MgB_4O_7$, $MgB_{10}O_{16}$, $MgSiO_3$, $MgMoO_4$, $Cu_2B_4O_7$, $Cu_2B_{10}O_{16}$, $Cu_2SiO_3$, $Cu_2MoO_4$, $CuB_4O_7$, $CuB_{10}O_{16}$, $CuSiO_3$, $CuMoO_4$, $SnB_4O_7$, $SnB_{10}O_{16}$, $SnSiO_3$, $SnMoO_4$, $Sn(B_4O_7)_2$, $Sn(B_{10}O_{16})_2$, $Sn(SiO_3)_2$ and $Sn(MoO_4)_2$.

10. A process according to claim 9 wherein the metal oxoanionic salt is selected from the group consisting of $Li_2MoO_4$, $Na_2MoO_4$, and $K_2MoO_4$.

11. A process according to claim 1 wherein the myrcene is in the form of a myrcene and limonene mixture.

12. A process according to claim 11 wherein the myrcene to limonene ratio is about 80 to about 20.

13. A process according to claim 1 further comprising contacting the myrcene with palladium (II) chloride in the presence of an oxidizing agent.

14. A process according to claim 13 wherein the oxidizing agent is a member selected from the group consisting of hydrogen peroxide, benzoquinone, a copper (II) salt, a cerium (IV) salt, an iron (III) salt and a silver (I) salt.

15. A process according to claim 14 wherein the oxidizing agent is a copper (II) salt or an iron (III) salt and said process is conducted in the presence of oxygen.

16. A process for producing citral comprising contacting a palladium-myrcene complex of the formula

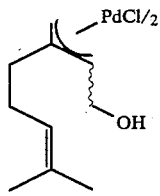

with a metal oxoanionic salt in the presence of an inert organic solvent.

17. A process according to claim 16 wherein the process is carried out at a temperature of at least about 80° C.

18. A process according to claim 17 wherein the process is carried out at a temperature of at least about 90° C.

19. A process according to claim 16 wherein the metal oxoanionic salt is selected from the group consisting of $Li_2B_4O_7$, $Li_2B_{10}O_{16}$, $Li_2SiO_3$, $Li_3PO_3$, $Li_2WO_4$, $Li_2CrO_4$, $Li_2MoO_4$, $LiTiO_3$, $LiCoO_2$, $Li_2CO_3$, $Li_2SO_4$, $Na_2B_4O_7$, $Na_2B_{10}O_{16}$, $Na_2SiO_3$, $Na_3PO_4$, $Na_2WO_4$, $Na_2CrO_4$, $Na_2MoO_4$, $NaTiO_3$, $NaCoO_2$, $Na_2CO_3$, $Na_2SO_4$, $K_2B_4O_7$, $K_2B_{10}O_{16}$, $K_2SiO_3$, $K_3PO_4$, $K_2WO_4$, $K_2CrO_4$, $K_2MoO_4$, $KTiO_3$, $KCoO_2$, $K_2CO_3$, $K_2SO_4$, $MgB_4O_7$, $MgB_{10}O_{16}$, $MgSiO_3$, $Mg_3(PO_4)_2$, $MgWO_4$, $MgCrO_4$, $MgMoO_4$, $Mg(TiO_3)_2$, $Mg(CoO_2)_2$, $MgCO_3$, $MgSO_4$, $CaB_4O_7$, $CaB_{10}O_{16}$, $CaSiO_3$, $Ca_3(PO_4)_2$, $CaWO_4$, $CaCrO_4$, $Ca(TiO_3)_2$, $Ca(CoO_2)_2$, $CaCO_3$, $CaSO_4$, $Cu_2B_4O_7$, $Cu_2B_{10}O_{16}$, $Cu_2SiO_3$, $Cu_3PO_4$, $Cu_2WO_4$, $Cu_2CrO_4$, $Cu_2MoO_4$, $CuTiO_3$, $CuCoO_2$, $Cu_2CO_3$, $Cu_2SO_4$, $CuB_4O_7$, $CuB_{10}O_{16}$, $CuSiO_3$, $Cu_3(PO_4)_2$, $CuWO_4$, $CuCrO_4$, $CuMoO_4$, $Cu(TiO_3)_2$, $Cu(CoO_2)_2$, $CuCO_3$, $CuSO_4$, $Ag_2B_4O_7$, $Ag_2B_{10}O_{16}$, $Ag_2SiO_3$, $Ag_2PO_4$, $Ag_2WO_4$, $Ag_2CrO_4$, $AgTiO_3$, $AgCoO_2$, $Ag_2CO_3$, $Ag_2SO_4$, $Al_2(B_4O_7)_3$, $Al_2(B_{10}O_{16})_3$, $Al_2(SiO_3)_3$, $AlPO_4$, $Al_2(WO_4)_3$, $Al_2(CrO_4)_3$, $Al_2(MoO_4)_3$, $Al(TiO_3)_3$, $Al(CoO_2)_3$, $Al_2(CO_3)_3$, $Al_2(SO_4)_3$, $SnB_4O_7$, $SnB_{10}O_{16}$, $SnSiO_3$, $Sn_3(PO_4)_2$, $SnWO_4$, $SnCrO_4$, $SnMoO_4$, $Sn(TiO_3)_2$, $Sn(CoO_2)_2$, $SnCO_3$, $SnSO_4$, $Sn(B_4O_7)_2$, $Sn(B_{10}O_{16})_2$, $Sn(SiO_3)_2$, $Sn_3(PO_4)_4$, $Sn(WO_4)_2$, $Sn(CrO_4)_2$, $Sn(MoO_4)_2$, $Sn(TiO_3)_4$, $Sn(CoO_2)_4$, $Sn(CO_3)_2$, $Sn(SO_4)_2$, $PdB_4O_7$, $PdB_{10}O_{16}$, $PdSiO_3$, $Pd_3(PO_4)_2$, $PdWO_4$, $PdCrO_4$, $PdMoO_4$, $Pd(TiO_3)_2$, $Pd(CoO_2)_2$, $PdCO_3$, $PdSO_4$, and $Pd(B_4O_7)_2$.

20. A process according to claim 19 wherein the metal oxoanionic salt is selected from the group consisting of $Li_2B_4O_7$, $Li_2B_{10}O_{16}$, $Li_2SiO_3$, $Li_2MoO_4$, $Na_2B_4O_7$, $Na_2B_{10}O_{16}$, $Na_2SiO_3$, $Na_2MoO_4$, $K_2B_4O_7$, $K_2B_{10}O_{16}$, $K_2SiO_3$, $K_2MoO_4$, $MgB_4O_7$, $MgB_{10}O_{16}$, $MgSiO_3$, $MgMoO_4$, $Cu_2B_4O_7$, $Cu_2B_{10}O_{16}$, $Cu_2SiO_3$, $Cu_2MoO_4$, $CuB_4O_7$, $CuB_{10}O_{16}$, $CuSiO_3$, $CuMoO_4$, $SnB_4O_7$, $SnB_{10}O_{16}$, $SnSiO_3$, $SnMoO_4$, $Sn(B_4O_7)_2$, $Sn(B_{10}O_{16})_2$, $Sn(SiO_3)_2$ and $Sn(MoO_4)_2$.

21. A process according to claim 20 wherein the metal oxoanionic salt is selected from the group consisting $Li_2B_4O_7$, $Li_2B_{10}O_{16}$, $K_2B_4O_7$ and $K_2B_{10}O_{16}$.

22. A process according to claim 16 wherein the inert aqueous organic solvent is selected from the group consisting of N-substituted aqueous pyrrolidones, N-substituted aqueous caprolactams, N,N-disubstituted aqueous acetamides, and substituted and unsubstituted toluene in water.

23. A process according to claim 22 wherein the solvent is an N-substituted aqueous pyrrolidone which is aqueous N-methylpyrrolidone.

24. A process according to claim 24 wherein the solvent is unsubstituted toluene in water.

* * * * *